US006866852B2

(12) United States Patent
Saitoh et al.

(10) Patent No.: US 6,866,852 B2
(45) Date of Patent: Mar. 15, 2005

(54) RECOMBINANT HERPESVIRUS OF TURKEYS AND USE THEREOF

(75) Inventors: Shuji Saitoh, Kanagawa (JP); Takashi Okuda, Tokyo (JP); Mayumi Kubomura, Kanagawa (JP); Kristi M. Dorsey, Lenexa, KS (US)

(73) Assignee: Zeon Corporation, Tokyo (JP)

( * ) Notice: Subject to any disclaimer, the term of this patent is extended or adjusted under 35 U.S.C. 154(b) by 0 days.

(21) Appl. No.: 10/059,152

(22) Filed: Jan. 31, 2002

(65) Prior Publication Data

US 2003/0157703 A1 Aug. 21, 2003

(51) Int. Cl.[7] .............................................. A61K 39/12
(52) U.S. Cl. .............................. 424/199.1; 424/204.1; 424/229.1; 435/69.1; 435/320.1
(58) Field of Search .................... 424/194.1, 204.1, 424/816, 229.1; 435/320.1, 41.1, 41.33, 69.1; 536/24.1, 23.72

(56) References Cited

FOREIGN PATENT DOCUMENTS

| EP | 1 026 246 A1 | 8/2000 |
|---|---|---|
| WO | WO 99/18215 * | 4/1999 |

OTHER PUBLICATIONS

Patent Abstract of Japan; Pub. No. 2001–000188;Sep. 1, 2001; full translation.

Saito et al.; U.S. Appl. No 09/509,871, filed Jul. 5, 2000 corresponding to WO99/18215.

K. Tsukamoto, et al.; "*Complete, Long–Lasting Protection against Lethal Infectious Bursal Disease Virus Challenge by a Single Vaccination with an Avian Herpesvirus Vector Expressing VP2 Antigens*"; Journal of Virology, vol. 76, No. 11, Jun. 2002, pp. 5637–5645.

* cited by examiner

*Primary Examiner*—Ali R. Salimi
(74) *Attorney, Agent, or Firm*—Armstrong, Kratz, Quintos, Hanson & Brooks, LLP (57) ABSTRACT

The present invention provides a recombinant herpesvirus of turkeys modified by the presence of cDNA encoding the F protein of Newcastle disease virus under the control of a promoter. The poultry vaccine consisting of the recombinant herpesvirus of turkeys of the present invention can induce in chickens protective immunity against Newcastle disease virus.

6 Claims, 5 Drawing Sheets

FIG. 1 Activities of Deleted Beta-actin Promoter

FIG.2

Construction of intermediate plasmid, pGIPecF, during the construction of homology plasmid, p45/46PecF.

FIG.3
Construction of homology plasmid, p45/46PecF

FIG.4

Western blot assay of rHVT/NDV, rHVT/NDV passage 5, and the HVT parent strain using NDV F rabbit antiserum. Lane 1 = CEF negative control; Lane 2 = HVT parent strain; Lane 3 = rHVT/NDV: Lane 4 = rHVT/NDV passage 5. An arrow indicates the F protein with a molecular weight of 60kDa..

Figure 5:
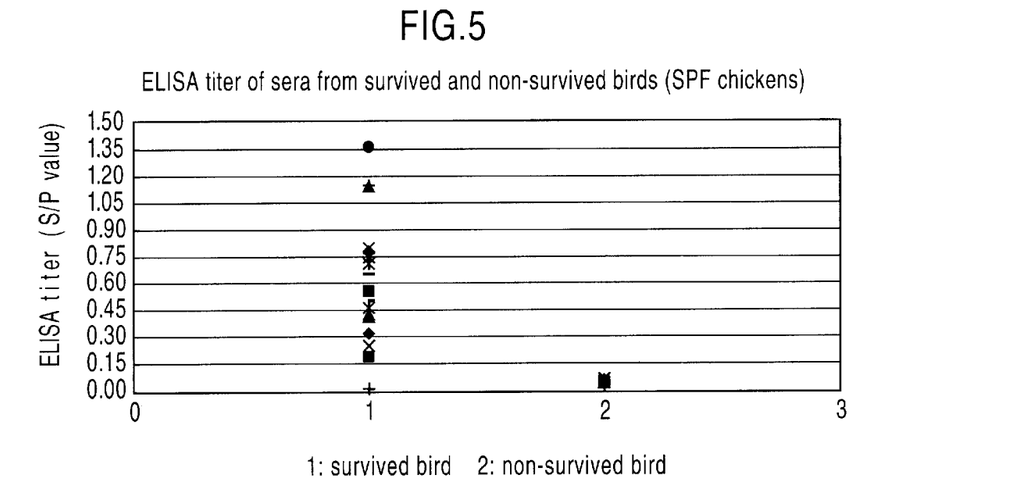
FIG. 5 shows an ELISA titer of survived and non-survived SPF chickens.
Figure 6:
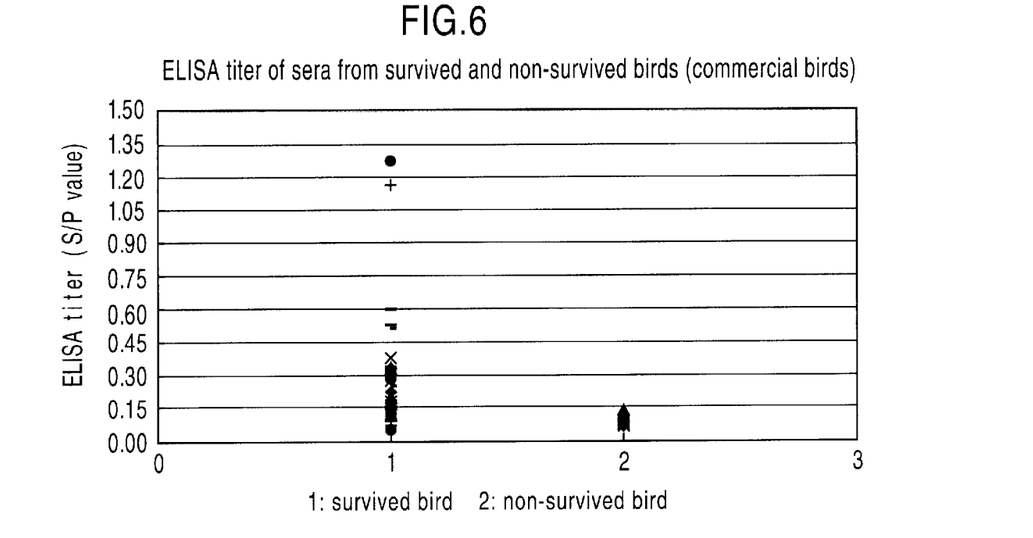
FIG. 6 shows an ELISA titer of survived and non-survived commercial birds.

FIGS.5 and 6 show the ELISA titers of survived and non-survived SPF and commercial birds, respectively. As indicated, all chickens having 0.15 or more of the antibody titer (S/P value) survived the virulent NDV challenge.

FIG.5

ELISA titer of sera from survived and non-survived birds (SPF chickens)

1: survived bird   2: non-survived bird

FIG.6

ELISA titer of sera from survived and non-survived birds (commercial birds)

1: survived bird   2: non-survived bird

RECOMBINANT HERPESVIRUS OF TURKEYS AND USE THEREOF

BACKGROUND OF THE INVENTION

1. Field of the Invention

The present invention provides a recombinant herpesvirus of turkeys (rHVT) comprising cDNA of the F protein (F gene) of Newcastle disease virus (NDV) under the control of a modified chicken beta-actin promoter.

2. Description of the Related Art

Newcastle disease is one of the most fearful contagious diseases in the poultry industry. Newcastle disease presents itself in many forms ranging from high mortality to an asymptomatic form. Strains are classified as (1) velogenic (high-virulence), (2) mesogenic (moderate-virulence), (3) lentogenic (low-virulence), and (4) asymptomatic (Alexander, D. J. In Diseases of Poultry 1997). Chickens infected with velognenic forms of NDV become gloomy and lethargic in a few days and the mortality rate is from dozens to more than fifty percent. Surviving birds often develop neurological symptoms such as wryneck or gyrospasm. One of the reasons the disease is so fearsome is that chickens are susceptible to NDV regardless of age and those infected with velogenic NDV show fulminant symptoms at all ages. Since NDV is highly transmissible, every chicken must be disposed of at the outbreak of the disease. The hennery should thoroughly be disinfected to prevent further infection. Strains in the mesogenic pathotype (moderate-virulence) are characterized by death in young chickens. Strains in the lentogenic pathotype (low-virulence) are characterized by mild respiratory infections and many of these strains are used to prepare vaccines for use in young chickens. Asymptomatic enteric strains are usually isolated from the gut of chickens showing no disease (Alexander, 1997). Newcastle disease affects both chickens and turkeys, however the clinical signs in turkeys are less severe than in chickens (Alexander, 1997).

At present, live and inactivated vaccines are available for the prevention of Newcastle disease. These vaccines are effective but not free from defect. The inactivated vaccine must be inoculated into breeder hens in lay, repetitively. The live vaccine is mainly for young chickens. However, long lasting immunity is not guaranteed for young chickens, which have high maternal antibody levels. Repeated administration of live vaccines is sometimes detrimental to the healthy growth of young chickens due to vaccine reactions causing mild respiratory disease. Thus, a new type of vaccine, which is efficacious, free from adverse effects, and does not require repeated administration, is desirable for the poultry industry.

To meet the industry's wishes, Sakaguchi et al. (J. Virol. 74:3217–3226, 2000; Vaccine 16:472–479, 1998) developed a recombinant Marek's disease virus serotype 1, which had the NDV F gene in the US10 region of the virus genome. The obtained recombinant virus induced lasting protective immunity against Newcastle disease in SPF chickens as well as in maternal antibody positive commercial birds.

Marek's disease is another serious problem for the poultry industry. Against this disease, herpesvirus of turkeys (HVT) (Witter R. L. et al. Am. J. Vet. Res. 1970, 31, 525–538) has been most widely used as a safe vaccine.

Until now, there have been several reports about the HVT-based Newcastle disease-Marek's disease bivalent vaccine. For instance, Morgan et al. (Avian Dis. 37:1032–1040, 1993; Vaccine 11:349–358, 1993; Avian Dis. 36:858–870, 1992) constructed recombinant HVTs having the NDV F gene and examined the efficacy of these recombinants as a Newcastle disease vaccine. Macmillan et al. (Vaccine 14:469–477, 1996) constructed recombinant HVTs expressing HN and F proteins of NDV and tested these recombinants for efficacy. In both cases, vaccinated SPF chickens were protected against NDV, but not satisfactorily commercial chickens having high maternal antibody levels Saitoh et al. inserted cDNA encoding F and HN proteins of NDV into the HVT genome (WO 99/18215). The inserted genes were under the control of the CMV or RSV promoter. The foreign gene insertion site was a newly identified intergenic region between UL44 and 45 or between UL45 and 46. These recombinants conferred good protection against NDV challenge in SPF chickens as well as in chickens with NDV maternal antibodies. However, these recombinants expressed two inserted genes of HN and F. Since HN protein induces heamagulutination inhibition (HI) antibodies to immunized chickens, it is difficult to distinguish vaccine immunized chickens and NDV infected chickens. Therefore, a recombinant virus expressing F protein gene, which induces an adequate protective immunity against Newcastle disease, is a more desirable vaccine. This objective was not easily attainable because rHVT having only F gene of NDV didn't induce desirable immunity in chickens as indicated by Morgan et al.

SUMMARY OF THE INVENTION

The present invention provides a recombinant herpesvirus of turkeys modified by the insertion of cDNA of the F protein of NDV under the control of a modified chicken beta-action promoter (Pec promoter). The rHVT induces long lasting protective immunity against NDV in SPF chickens as well as in commercial chickens that have high maternal antibody to NDV.

Specifically, the present invention provides a recombinant herpesvirus of turkeys modified by the insertion of the NDV F gene under the control of a promoter, of which sequence is described in SEQ NO.1. The present invention further provides a Newcastle Disease-Marek's Disease bivalent vaccine consisting mainly of the said recombinant herpesvirus of turkeys.

The present invention is described below in more detail.

SEQ ID NO.1
5'-AGTTATTAATAGTAATCAATTACGGGGTCATTAGTTCATAGCCCATA

TATGGAGTTCCGCGTTACATAACTTACGGTAAATTGGCCCCGCCGGCTGA

-continued
CCGCCCACGACCCCCGCCCATTGACGTCAATAATGACGTATGTTCCCATA

GTAACGCCAATAGGGACTTTCCATTGACGTCAATGGGTGGAGTATTTACG

GTAAACTGCCCATTGGCAGTACATCAAGTGTATCATATGCCAAGTACGCC

CCCTATTGACGTCAATGACGGTAAATGGATGCAGTATTTTGTGCAGCGAT

GGGGCGGGGGGGGGGGGGGGCGCGCGCCAGGCGGGGCGGGGCGGGGC

GAGGGGGCGGGCGGGCGAGGCGGAGAGGTGCGGCGGCAGCCAATCAGA

GCGGCGCGCTCCGAAAGTTTCCTTTTATGGCGAGGCGGCGGCGGCGGCGG

CCCTATAAAAAGCGAAGCGCGCGGCGGGCGGGAGTCGCTGCGCGCTGCCT

TCGCCCCGTGCCCCGCTCCGCCGCCGCCTCGCGCCGCCCGCCCCGGCTCT

GAGTGACCGCGTCTAGAGG-3'

(NDV F gene)

As long as encoding the NDV F protein, any gene from any NDV strain is appropriate for the purpose of the present invention. The F gene of Sato, Miyadera, D26, Atami, or Fuji as well as of Texas GB, B1, or LaSota strain is an example. The F gene of a field isolate or of any known DNA sequence is also appropriate. Among these, the gene from D26 is a favorable example. Incorporating an additional antigen gene into the backbone virus is not desirable for the purpose of the present invention.

(Promoter)

In the present invention, the NDV F gene is controlled by a promoter described in SEQ NO.1 (designated Pec promoter) or that homologous to it. The Pec promoter (Japanese Unexamined Patent Publication No. 2001-188) is generated by deleting a dispensable region of the chicken beta-actin promoter. A promoter homologous to Pec means a promoter of which activity is nearly equal to that of Pec and of which length is 120 to 850 base pair (bp) or more favorably 150 to 600 bp. A homologous promoter can be generated by substitution, deletion, or addition of nucleotides of to the beta-actin promoter. The promoter used in the present invention may include a naturally occurring or modified enhancer sequence. An example of such a promoter is COA promoter described in SEQ NO.2.

(Avian Herpesvirus)

As long as being non-pathogenic to chickens, any herpesvirus of turkeys can be used in the present invention. For instances, FC126 (ATCC VR-584B), PB-THV1, H-2, YT-7, WTHV-1, or HPRS-26 strain is suitable for the backbone virus. Among these, FC126 is favorably used in the present invention because of its safe use in chickens.

(Region for Gene Insertion)

Several non-essential regions of HVT are known, which are dispensable for virus growth and suitable for NDV F gene insertion. For instance, UL43 (WO 89/01040), US2 (WO 93/25665) or inter-ORF region between UL44 and UL46 (WO 99/18215) is appropriate for the insertion of the F gene. Among these, the inter-ORF region between UL44 and UL46 is most suitable. For the present invention, a non-essential region can newly be identified by the following general procedure. First, avian herpesvirus DNA fragments of appropriate length are cloned into an E. coli plasmid and physically mapped by restriction enzyme analysis. Then a gene cassette consisting of a promoter and a marker gene is inserted into an appropriate restriction site of the cloned DNA fragment resulting in a homology plasmid. As described later, if the homologous recombination with the obtained homology plasmid resulted in a recombinant virus expressing the inserted marker gene and if it were stable in vitro and in vivo, the originally selected DNA fragment should be a non-essential region suitable for NDV-F cDNA insertion.

(Construction of rHVT)

For the present invention, any known method of generating the recombinant avian herpesvirus is applicable. A typical example is as follows. (1) First, as described above, a recombinant plasmid is constructed, which includes a non-essential region of the avian herpesvirus. Then, preferably with a promoter at the 5' terminus and a polyadenlyation signal at the 3' terminus, NDV-F cDNA is inserted into the said non-essential region to generate a homology plasmid. (2) The resultant plasmid is transfected into chicken embryo fibroblast (CEF) cells infected with parent HVT or co-transfected into CEF cells with infectious HVT genomic DNA. Transfection is performed by any known method (3) The transfected CEF cells are inoculated into culture plates and incubated till the virus plaques become visible. (4) The identifiable plaques include recombinant viruses as well as parent wild-type viruses. The recombinant virus is purified from wild type virus by any known method to screen expression of inserted foreign genes.

(Newcastle Disease-Marek's Disease Bivalent Vaccine)

Since the F protein is a protective antigen of NDV and the backbone HVT is a live Marek's disease vaccine, rHVT containing the F gene of the present invention may be used bivalent vaccine against Newcastle and Marek's diseases or as monovalent vaccine against Newcastle disease.

The vaccine consisting mainly of rHVT of the present invention may include chicken cells and/or ingredients of culture media. As long as not pharmacologically detrimental, the vaccine may contain any ingredients such as preservatives. In addition, the vaccine of the present invention can be used as a mixture with any recombinant or non-recombinant viruses such as the MDV serotype 1 or serotype 2 vaccine strains.

Any known method is applicable to the preparation of the recombinant bivalent vaccine of the present invention. For instance, rHVT is inoculated into permissive culture cells such as CEF cells and grown to an appropriate titer. Then, the cells are scraped off from culture plates or bottles by scraper or by trypsin treatment and subjected to centrifugation. Cells separated from the supernatant are then suspended in the culture medium containing dimethyl sulfoxide and stored in liquid nitrogen. When rHVTs are in the supernatant, they are collected and lyophilized.

The bivalent recombinant HVT vaccine is administered to chickens by any known method of inoculating Marek's disease vaccine. For instance, the vaccine of the present invention is diluted to give $10-10^5$, or more favorably $10^2-10^4$ plaque forming units (PFU)/dose, and inoculated into subcutaneously behind the neck of one day of age chickens or into embryonating eggs by syringe or by any apparatus for injection.

The present avian bivalent vaccine gives SPF chickens 90% or more protection against the NDV challenge and at least 70% or more protection to the commercial chickens having a significant level of anti-NDV maternal antibody.

In the present invention, protection against NDV challenge is determined by the ratio of protected birds to total tested birds in the challenge testing as described in the examples. First, the appropriate dose of the NDV challenge virus is determined by challenging non-vaccinated birds. 90% or more of these birds (the negative control group) must show clinical signs. Next, the vaccinated birds are challenged with the same dose of the challenge virus by intramuscular route to the femoral region, or by intra-tracheal, intra-ocular, or infraorbital sinus route. The challenged birds were observed for onset of Newcastle disease, specificly neurological symptoms.

DESCRIPTION OF THE PREFERRED EMBODIMENTS

EXAMPLE 1
Construction of the Homology Vector

The plasmid construction was essentially performed by the standard molecular biology techniques (Molecular Cloning: A Laboratory Manual. 2nd Edition, Cold Spring Harbor Laboratory, Cold Spring Harbor, N.Y. 1989). DNA restriction fragments were electrophoresed on agarose gels and purified with QIAquick Gel Extraction Kit (QIAGEN, Cat # 28704).

1-1 Construction of the Plasmid Used for the Measurement of the Promoter Activity Plasmid pGIMICSpolyASfi (2773 bp, WO 99/18215) was generated by introducing a polyadenylation signal and a SfiI site into the multi-cloning site of pUC18. pGIMICSpolyASfi was then digested with NheI and ligated with the 1721 bp fragment which was excised from Pica gene Enhancer2 (5064 bp, TOYO INK MFG. CO., LTD.) by NheI and XbaI digestion. The obtained plasmid was designated pLUC-Pro (4494 bp).

Next, a DNA fragment (about 1.5 kilobases) including the beta-actin promoter was prepared by PCR using a chicken cell genomic DNA bank as a template. The primers were PrBac1 (SEQ ID NO. 2, 5'-CAGTGTCGCTGCAGCTCAGTGCATGCACGCTCATTGCCC-3') and PrBac2 (SEQ ID NO. 3, 5'-GCTCTAGAGTCGACAAGCTTCATGGCTGGCTGCGGAGGAACAGAGAAGGG-3').

The obtained fragment was digested with PstI and XbaI and ligated with the 4482 bp fragment generated by digesting pLUC-Pro with PstI and XbaI. The resultant plasmid, designated pLUC-bac, was 5986 bp long and included the beta-actin promoter region.

pLUC-bac was digested with BamHI and BglII and the resulting 5958 bp fragment was self-ligated to yield pLUC-bac-Sma. Since pLUC-bac-Sma had PstI and SmaI sites upstream of the beta-actin promoter, restriction of pLUC-bac-Sma with PstI and SmaI followed by self-ligation yielded the first plasmid to obtain the shortened 5'-region of the beta-actin promoter. Similarly, restriction of pLUC-bac with SacI and XbaI followed by self-ligation generated the second plasmid to obtain the shorted 3'-region of the beta-actin promoter. The resultant two plasmids were then linearized and subjected to the ExoIII treatment using Kilo-Sequence Deletion Kit (TAKARA SYUZO CO., LTD.). Sampling was performed at one, two, and three minutes to obtain 7 samples from the first plasmid and 22 from the second. All 29 fragments included about 200 to 1500 bp promoter region. The obtained fragments were blunt-ended and self-ligated by the standard procedure to generate the circular plasmids.

The measurement of the luciferase activity was performed with PicaGene (TOYO INK MFG. CO., LTD.). Briefly, one μg each of 29 plasmids was introduced into CEF cells by electroporation using Gene Pulser (Bio-Rad Laboratories). Cells were then cultured for 24 hours, and cell lysis buffer (included in PicaGene kit) was added. The cells were frozen for one hour at −80° C., and thawed at room temperature to comp ete the cell lysis. After centrifugation, 10 μl of the recovered supernatant was added to 100 μl of the PicaGene substrate solution and one minute later, intensity of luminescence (Unit: RLU) was measured with Lumino- Meter (Model 11253, Bio-Rad Laboratories). The Lumino-Meter was used to calculate the amount of the produced luciferase, an indicator of the promoter activity (see FIG. 1).

As shown in FIG. 1, among the samples having a deletion towards 5'-terminus, those lacking more than 120 bp upstream of the TATAAA box showed a drastic decrease in promoter activity. On the contrary, there was no co-relation between the promoter activity and the length of the deletion towards the 3'-terminus. For instance, a deletion of about 100 bp incurred about a one-fifth decrease in the promoter activity when compared with that of the full length beta-actin promoter. Further deletion (greater than 100 bp) towards the 3'-terminus did not regain the original activity.

1-2 Core Sequence Promoter

References from the literature (Ref. 12–19) indicate all regions of the beta-action promoter are not indispensable. Based on this information, 273, 211, 175, and 163 bp fragments were obtained by PCR using the beta-actin promoter of pLUC-bac as a template. Primers were SEQ NO. 4 (5'-TATTTTGTGCAGCGAT-3') and SEQ NO. 5 (5'-ACGTCTAGAAGGCAACGCAGCGACT-3'), or SEQ NO. 4 and SEQ NO. 6, (5'-CTGTCTAGATAACGCGGTCAGTCAGA-3'). The obtained fragments coa273, coa211, coa175 and coa163 were called Core Sequence Promoters (COAs).

Next, these four COAs were digested with PstI and XbaI and resulting fragments were ligated with a fragment of 4482 bp, which was excised from pLUC-pro with PstI and XbaI. The promoter activity of these four plasmids was measured as described in Example 1-1. In consequence, the activity of pULC-COA273, pULC-COA211, pULC-COA175 and pLUC-COA163 was 97%, 76%, 96%, and 34%, respectively, of that of the full-length beta-actin promoter. The promoter included in pULC-COA273 was designated the COA Promoter, since it showed the highest promoter activity.

1-3 Construction of p45/46Sfi (FIGS. 2 & 3)

Based on the information of the gC homologue (gCh) gene of MDV serotype 1 (Coussens et al., J. Virol. 62:2373–2379, 1988) and its adjacent BamHI-B fragment (Japanese Unexamined Patent Publication No. H6-292583), a DNA fragment having an SfiI site between two ORFs UL45h and UL46h, was prepared by PCR and cloned into pUC18. First, HVT DNA was prepared from CEF cells infected with the HVT FC126 strain according to the method of Lee et al. (J. Gen. Virol., 51: 245–253, 1980). Using the obtained HVT DNA as a template, PCR was performed with two pairs of primers. The first pair was SEQ NO. 7 (5'-CCCCGAATTCATGGAAGAAATTTCC-3') and SEQ NO. 8 (5'-CGCGGGCCTTATTGGCCAAAACACACCTCTAACGGTTACT-3'). The second pair was SEQ NO. 9 (5'-GCGCGGCCAATAAGGCCAAAACACAGTAACCGTTAGAGGT-3') and SEQ NO. 10 (5'-CCCCAAGCTTTCAAGTGATACTGCGTGA-3'). Using the mixture of the obtained two PCR products as template, another PCR was conducted with SEQ NO. 7and SEQ NO. 8 to generate a fragment having an SfiI site between two ORFs UL45h and UL46h.

The resulting fragment was then digested with EcoRI and HindIII and ligated to pUC18, which had been digested with EcoRI and HindIII. The obtained plasmid was designated p45/46Sfi.

1-4 Construction of pUC18polyASfi

Plasmid pUC18polyASfi was constructed by annealing two synthetic oligonucleotides (SEQ NO. 11 and SEQ NO. 12) followed by ligation to pUC18, which had been digested with EcoRI and HindIII.

SEQ NO. 11
138bp:
5'-AGCTTGCCAATAAGGCTGCAGGTCGACTCTAGAGGATCCCCGGGCGA

GCTCGCTAGCGGGCCCGCATGCGGTACCGTCGACAATAAAGAACCGCTT

TAAGAATAGTGTTTATTTTTGTGTTTATGGCCAATAAGGCCG-3'
SEQ NO. 12
138bp:
5'-AATTCGGCCTTATTGGCCATAAACACAAAAATAAACACTATTCTTAA

AGCGGTTCTTTATTGTCGACGGTACCGCATGCGGGCCCGCTAGCGAGCT

CGCCCGGGGATCCTCTAGAGTCGACCTGCAGCCTTATTGGC-3'

The inserted fragment was excised by BglI and the cohesive ends were designed to be inserted into the SfiI site of p45/46Sfi. In addition, a multi-cloning site was added to the 5'-terminus of the fragment so that a promoter-foreign gene cassette could be inserted. The 43 bp sequence downstream from the SalI site was polyadenlyation signal, which was derived from the sequence located downstream of UL46h of the MDV GA strain.

1-5 Construction of pBac

An DNA fragment of about 1.5 kilobases (kb) including the beta-actin promoter described in EXAMPLE 1-1 was digested with PstI and SalI and ligated with pUC18polyASfi, which had been digested with PstI and SalI. The obtained plasmid was designated pBac.

1-6 Construction of pGICOA

Using pBac as a template, PCR was performed with primers PrBac3 and PrBac4.

(SEQ NO. 13)
PrBac3:
5'-TTTCTGCAGTATTTTGTGCAGCGAT-3'
(SEQ NO. 14)
PrBac4:
5'-CTGTCTAGATAACGCGGTCAGTCAGA-3'

PrBac3 has a PstI site and PrBac4 has an XbaI site. The PCR-amplified fragment was excised with PstI and XbaI to generate a fragment of about 300 bp. The fragment was then ligated to pUC18polyASfi, which had been digested with PstI and XbaI. The obtained plasmid was designated pGICOA.

1-7 Construction of Pec Promoter

The CMV enhancer was added to the COA promoter to enhance its promoter activity.

Since the CMV enhancer had two BglI sites, a BglI cassette from the CMV enhancer was not easily inserted into the SfiI site of pGICOA. To delete BglI sites, in vitro mutagenesis was conducted by PCR with three pairs of primers using pBK-CMV (Stratagene) as a template. The primers were PrCMV1 (SEQ NO. 15) and PrCMV3 (SEQ NO. 17), PrCMV4 (SEQ NO. 18) and PrCMV5 (SEQ NO. 19), and PrCMV6 (SEQ NO. 20) and PrCMV2 (SEQ NO. 16). Using the obtained three amplified fragments as a template, the secondary PCR was performed with primers PrCMV1 and PrCMV2. Since PrCMV1 had a PstI site and PrCMV2 had an EcoT22I site, the amplified fragment was digested with PstI and EcoT22I to yield a fragment of about 300 bp, which was in turn cloned into the PstI site of pGICOA to generate pGIPec. The promoter included in pGIPec, designated Pec promoter, consisted of about 275 bp fragment from the CMV enhancer followed by a 273 bp fragment from the beta-actin promoter. The Pec promoter showed enhanced promoter activity, 6.5 times higher than that of COA promoter when evaluated in vitro as described in Example 1-1.

(SEQ No. 15)
PrCMV1:
5'-GGG CTG CAG AGT TAT TAA TAG TAA TCA ATT-3'
(SEQ No. 16)
PrCMV2:
5'-GGG ATG CAT CCA TTT ACC GTC ATT GAC GTC-3'
(SEQ No. 17)
PrCMV3:
5'-GGG TCG TTG GGC GGT CAG CCG GCG G-3'
(SEQ No. 18)
PrCMV4:
5'-CTT ACG GTA AAT GGC CCG CCT GCT G-3'
(SEQ No. 19)
PrCMV5:
5'-TAC ACT TGA TGT ACT GCC AAT GGG C-3'
(SEQ No. 20)
PrCMV6:
5'-TAT TTA CGG TAA ACT CCC CAT TGG C-3'

1-8 Construction of NDV-F Vector

Using XLIII10H (Sato, H. et al., Virus Research, 7241–7255, 1987) as a template, PCR was performed with primers PrF1 and PrF2.

(SEQ No. 21)
PrF1:
5'-GCTCTAGAGGATCCGCATGGGCTCCAGATCTTCTACCAGGATCCC-3'
(SEQ No. 22)
PrF2:
5'-GCGAGCTCGGTCCATGACTGAAGACTGCTATTGG-3'

PrF1 has XbaI and BamHI sites. PrF2 has a SacI site.

The amplified fragment of about 1.9 kb long encoded 553 amino acids of the F gene, which was identical to that reported in Virus Research, 7241–7255, 1987. The fragment was digested with XbaI and KpnI and cloned into pGIPec, which had been digested with XbaI and KpnI. The obtained plasmid was designated pGIPecF.

1-9 Construction of the Homology Vector p45/46PecF

For construction of the homology plasmid, p45/46pecF, the Pec promoter, the NDV F gene and the SV40 polyadenylation signal sequence was inserted in p45/46Sfi. First, the Pec promoter and the NDV F gene were excised from pGIPecF with BglI and KpnI. Second, the SV40 polyadenylation signal sequence was amplified from pBR-CMV (Stratagene) by PCR and cut with BglI and KpnI. These two fragments were cloned into the SfiI site disrupting one of the SfiI sites and resulting in the homology plasmid, p45/46pecF.

EXAMPLE 2

Construction and Purification of rHVT/NDV

Viral DNA of the HVT wild type, FC126 strain (wt-HVT) was prepared as described by Morgan et al. (Avian Diseases, 34:345–351, 1990). The CEF cells were transfected with the prepared wt-HVT DNA and p45/46PecF (see Example 3-3). The resulting recombinant virus was plaque purified by staining plaques with the anti-NDV-F antibody.

Briefly, 5 μg of the homology vector p45/46PecF and 25 μg of wt-HVT DNA were dissolved in 100 μl of Saline G (0.14 M NaCl, 0.5 mM KCl, 1.1 mM $Na_2HPO_4$, 1.5 mM $NaH_2PO4$, 0.5 mM $MgCl_2$, 0.011% glucose). Next, CEF cells were suspended in 0.7 ml of Saline G and subjected to electroporation. Transfected cells were incubated for 10 minutes at room temperature and transferred to a 60-mm dish, which contained 5 ml medium consisting of Leibovitz's L-15 (GIBCO BRL, Cat. #41300-39) and McCoy's 5A Medium (GIBCO BRL, Cat. #21500-061) (1:1) and 4% calf serum (LM (+) medium). After incubating at 37° C. in 5% $CO_2$, recombinants were purified from wt-HVT by a series of limiting dilutions. Expression of the F gene was confirmed at each round of purification using an antigen-antibody reaction using the anti-NDV-F monoclonal antibody 3-1G/5 (Morrison, T. G., Proc. Natl. Acad. Sci. U.S.A. 84: 1020–1024, 1987) as the primary antibody. The purification procedure was repeated until every obtained plaque was stained positively by the anti-NDV-F antibody. The purified recombinant HVT was designated rHVT/NDV.

EXAMPLE 3
Verification of the Stability of rHVT/NDV
3-1 Southern Hybridization

The purified rHVT/NDV was propagated on CEF cells of two 150-mm dishes to obtain confluent plaques. Cells were recovered from dishes by scraping, transferred to Falcon tubes and centrifuged at 1,500 revolutions per minute (rpm) for 5 minutes. Harvested cells were washed with phosphate buffered saline (PBS), re-suspended in 1.2 ml of PBS and 0.8 ml of a lysis buffer (1.25% TritonX-100, 250 mM 2-ME, and 50 mM EDTA in PBS) and lysed by vortexing for 30 seconds. The lysates were then centrifuged at 3,000 rpm for 5 minutes at room temperature and the supernatant was transferred to an Eppendorf tube. The viruses were collected by centrifugation at 15,000 rpm, 22° C. for 20 minutes. The recovered pellets were then suspended in 1 ml of 12.5 mM Tris-Cl (pH 7.5) supplemented with 4 $\mu$l of a nuclease solution (0.25 mg/ml DNase 1, 0.25 mg/ml RNase A, 150 mM NaCl), incubated at 37° C. for 30 minutes, and disrupted by incubating at 55° C. for 30 minutes with a SDS-protease solution (500 mM EDTA, 25 $\mu$l; 10% SDS, 125 $\mu$l; $H_2O$, 87 $\mu$l; 10 mg/ml Protease K, 12.5 $\mu$l; 2-Mercaptoethanol, 0.5 $\mu$l). The obtained mixture was treated twice with phenol-chloroform, and 16 $\mu$l of 5M NaCl was added to the aqueous phase. The viral DNA was precipitated by adding 2.5 volumes of −20° C. ethanol, washed with 70% ethanol and centrifuged. After air-drying, the recovered pellets were dissolved in 50 $\mu$l of TE buffer (10 mM Tris-Cl (pH 8.0), 1 mM EDTA).

The recovered viral DNA in TE buffer was then digested with XhoI, XbaI, and SfuI and subjected to 0.8% agarose gel electrophoresis. The electrophoresed DNA fragments on the single gel were transferred simultaneously to two nylon membranes (Molecular Cloning: A Laboratory Manual, third edition, 6.35, Sambrook, J., and Russell, D. W. Cold Spring Harbor Laboratory). After fixing DNA by baking, the immobilized DNA was hybridized with a DIG-labeled probe, "F probe" or "IS45/46 probe", which was prepared with PCR DIG Probe Synthesis Kit (ROCHE DIAGNOSTICS, Cat. #1636090). The F probe was prepared by PCR with NDV-F-F (SEQ ID NO. 23) and NDV-F-R (SEQ NO. 24) as primers and p45/46PecF as a template. IS45/46 probe was prepared with 45/46-F (SEQ NO. 25) and 45/46-R (SEQ NO. 26) and p45/46Sfi.

```
NDV-F-F □SEQ NO. 23□
5'-CTAGCAGTGGCAGTTGGGAAGAT-3'

NDV-F-R □SEQ NO. 24□
5'-GTTAAGGCAGGGGAAGTGATTTGT-3'

45/46-F □SEQ NO. 25□
5'-GGGGAAGTCTTCCGGTTAAGGGAC-3'

45/46-R □SEQ NO. 26□
5'-GGTGCAATTCGTAAGACCGATGGG-3'
```

The results of southern blotting showed that a 3.6 kb fragment hybridized to the F probe and 3.6 and 1.2 kb fragments hybridized to the IS45/46 probe, indicating that the obtained rHVT/NDV had the expected genomic structure.

3-2 In vitro Stability of rHVT/NDV rHVT/NDV was passaged ten times in CEF cells and subjected to Southern blot analysis. The results were the same with those obtained in Example 3–1, indicating that rHVT/NDV of the present invention was stable even after the 10 passages.

3-3 In vivo Stability of rHVT/NDV

3000 PFU of rHVT/NDV was inoculated subcutaneously into the back of the SPF chicken or of commercial chicken having the anti-NDV maternal antibody. At week 3, 4, 5, and 6 post vaccination, peripheral blood was collected from the vaccinated birds and viruses were recovered from lymphocytes in the peripheral blood. Harvesting the lymphocytes was performed as follows.

Using a 2.5 ml syringe containing 0.5 ml of a heparin solution (100 u/ml), 2 ml of blood was collected from chickens and placed over 5 ml of Ficoll-Paque (Amersham-Pharmacia) in a 15 ml Falcon centrifuge tube. After centrifugation at 1800 rpm for 20 minutes, a band of peripheral blood lymphocytes was formed at the boundary between the Ficoll-Paque and serum layers. The boundary layer was collected with a Pasteur pipette, inoculated into CEF cells in a 9 cm dish and cultivated for seven days. Isolation of viruses from lymphocytes was considered successful when plaques were observed during the process of the first cultivation followed by the subcultivation. The results were summarized in Table 1.

TABLE 1

| | Isolation of rHVT from peripheral blood lymphocytes of vaccinated birds | | | | |
|---|---|---|---|---|---|
| | rHVT/NDV | | HVT FC126 | | Non-vaccinated |
| | MA+*** | SPF**** | MA+ | SPF | MA+ |
| 3 wks** | 2/2* | ND***** | 2/2 | 1/1 | ND |
| 4 wks | 3/3 | 2/2 | 1/3 | 2/2 | 0/2 |
| 5 wks | 3/3 | 2/2 | 1/3 | ND | 0/2 |
| 6 wks | 3/3 | 2/2 | 1/3 | 2/2 | 0/2 |

*Number of birds from which the virus was recovered / Number of tested birds
**Weeks of age
***Maternal antibody positive chicken
****Specific pathogen free chicken
*****Not done As shown in Table 1, rHVT/NDV as well as the parent HVT FC126 strain was recovered from peripheral blood lymphocytes of vaccinated chickens from three to six weeks post inoculation. When stained with the anti-F antibody as described in Example 2, all recombinant plaques were shown to express the F gene, indicating that rHVT/NDV was stable after in vivo passage.

EXAMPLE 4

Verification of the Inserted Gene Expression by rHVT/NDV 4-1 Immunofluorescence Technique rHVT/NDV-infected cells were incubated with fresh CEF cells in tissue culture chamber slides at 37° C. and obtained plaques were fixed with cold acetone. To detect the expressed antigen gene products, the chicken anti-NDV antiserum or rabbit anti-F antiserum was used in the 500-fold dilution in PBS as the primary antibody. Fixed cells were incubated with the primary antibody at room temperature in 100% humidity for about one hour, washed three times with PBS, and reacted with the secondary antibody for about one hour at room temperature. The anti-chicken immunoglobulin or anti-rabbit IgG antibody, which was labeled with a fluorescent substance (FITC), was used as the secondary antibody. After washing three times with PBS, the treated slides were inspected by fluorescence microscopy. Cells infected with parent HVT FC-126 were used as a control. The results were summarized in Table 2.

TABLE 2

Expression of the inserted F gene by rHVT/NDV
(Detection of fluorescence)

| Virus | Primary antibody | | | |
|---|---|---|---|---|
| | rabbit anti-F antiserum | chicken anti-NDV antiserum | anti-VP2 monoclonal antibody □R63□ | PBS |
| rHVT/NDV | + | + | − | − |
| FC126 | − | − | − | − |
| None | − | − | − | − |

+: detected, −: not detected

As Shown in Table 2, rHVT/NDV Expressed the Inserted NDV-F Gene.

4-2 Western Blotting

Figure 1:
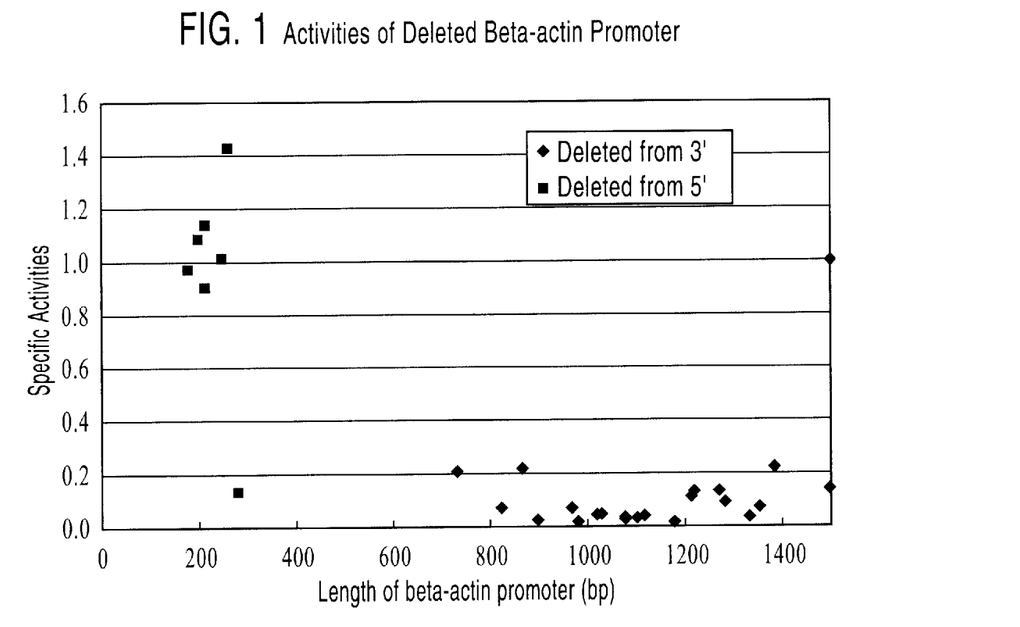
FIG. 1 shows a plot of activities of deleted beta-actin promoter.
Figure 2:
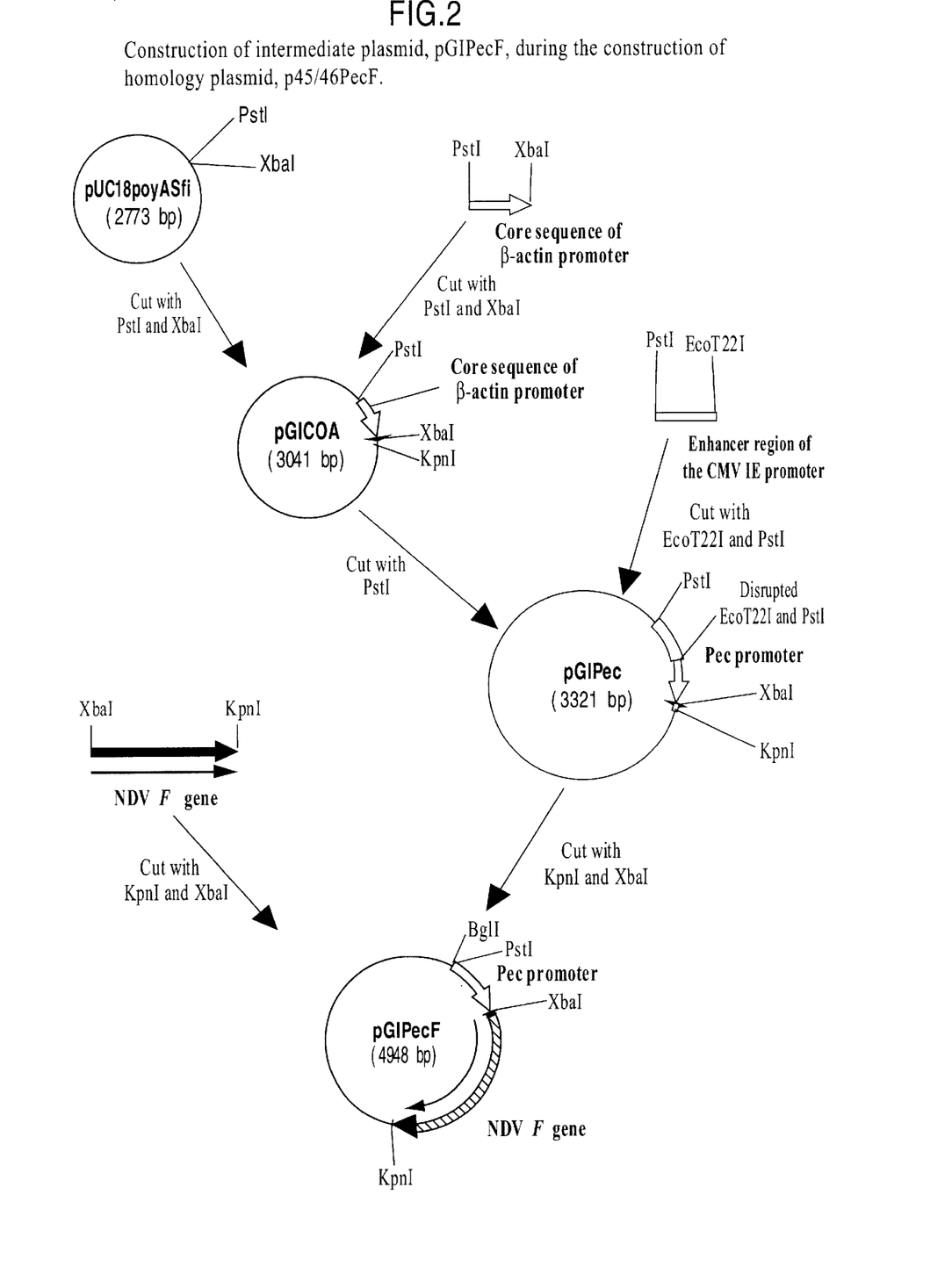
FIG. 2 shows a schematic diagram of construction of intermediate plasmid pGIPecF.
Figure 3:
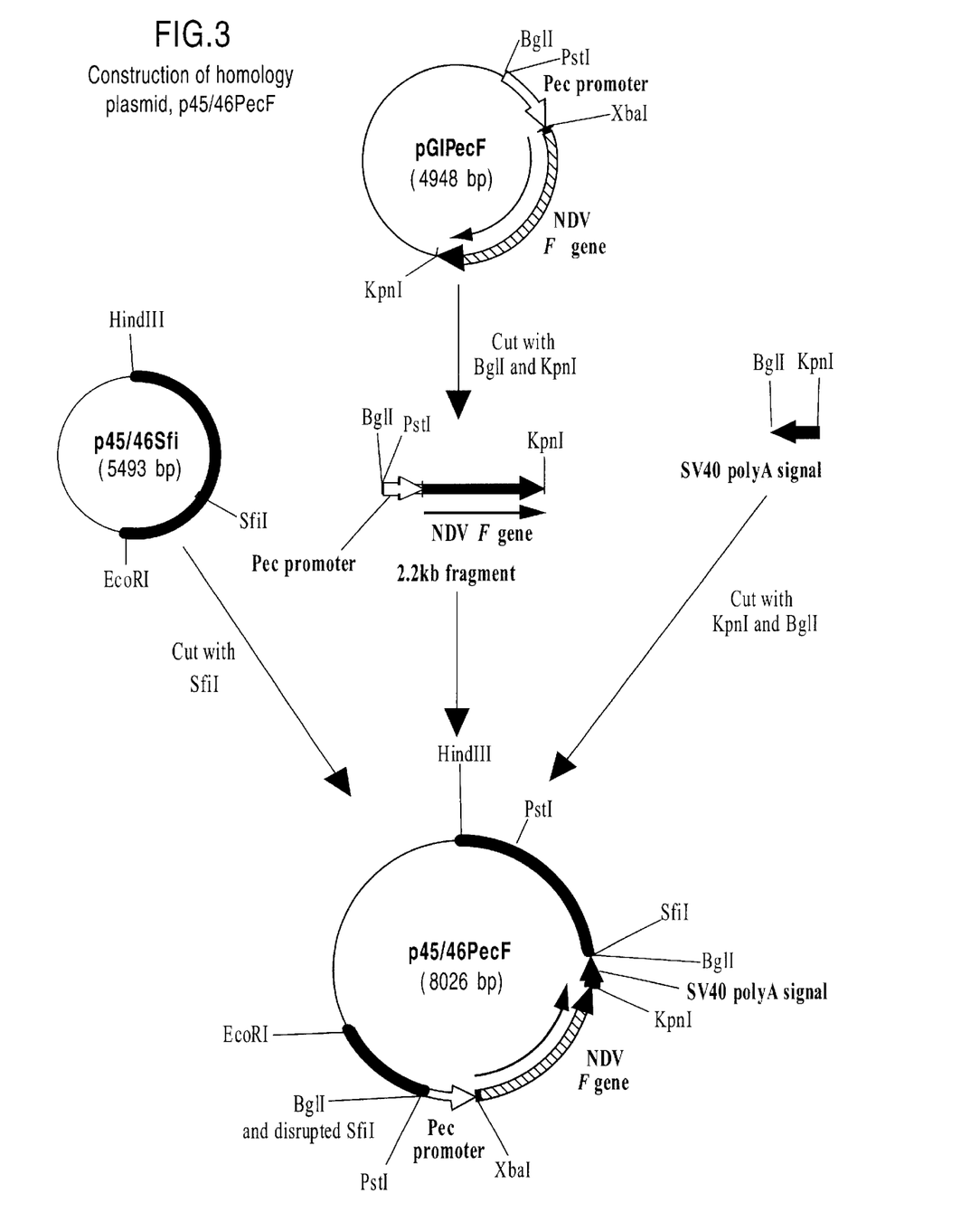
FIG. 3 shows a schematic diagram of construction of homology plasmid p45/46PecF.
Figure 4:
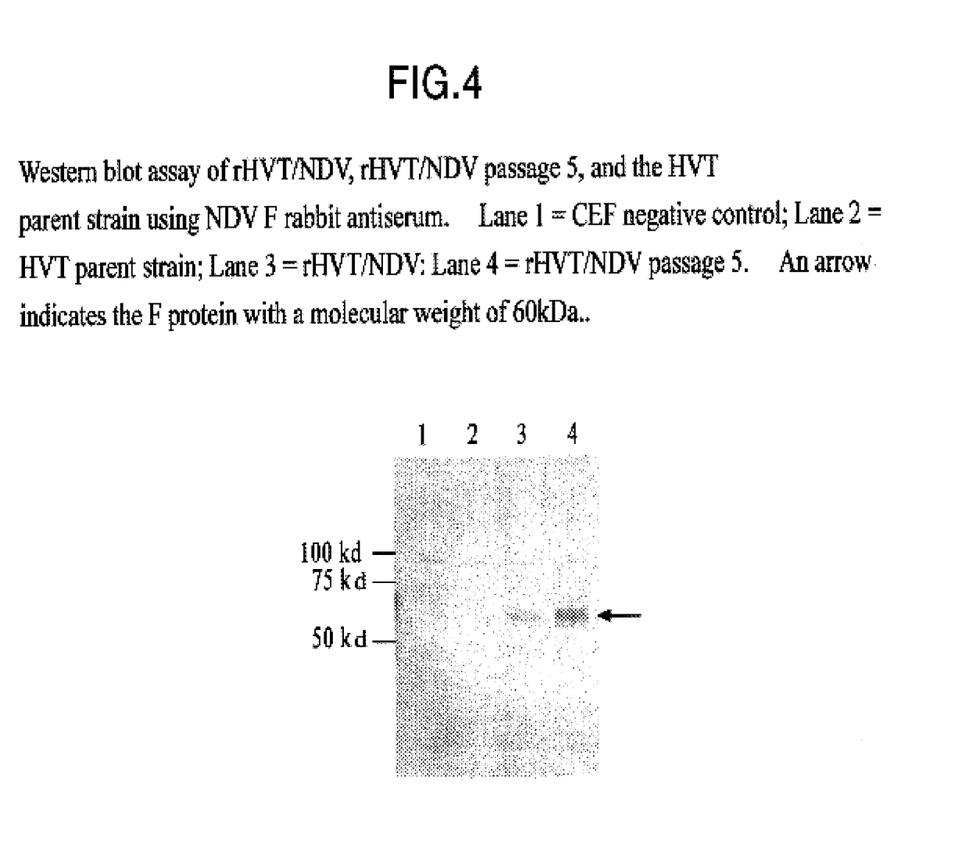
FIG. 4 shows a Western blot assay.

CEF cells were infected with rHVT/NDV at m.o.i.=0.1, incubated for 72 hours, and solubilized in a SDS-GEL loading buffer. Similarly, cells infected with parent HVT FC126 or non-infected cells were incubated and solubilized. The obtained samples were reduced, denatured, and subjected to SDS-PAGE. The electrophoresed proteins were transferred from SDS-GEL to a PVDF membrane (Immobilon-P, Millipore), which was blocked in 1% w/v non-fat milk powder in PBS at room temperature for one hour. The treated membrane was then reacted with the anti-F rabbit antiserum in 500-fold dilution at room temperature, washed three times with PBS, and incubated for one hour with the biotinylated anti-rabbit goat antiserum. After washing three times with PBS, the membrane was incubated for one hour with an avidin-alkaline phosphatase complex, washed three times with PBS and one time with TBS, and reacted with BCIP-NBT (a substrate of alkaline phosphatase.) As shown in FIG. 4, a protein band of 60 kilodaltons (kDa) was observed only in the lane with rHVT/NDV infected cells, which was the expected size of the F protein.

EXAMPLE 5

Efficacy of rHVT/NDV in SPF Chickens rHVT/NDV obtained in Example 2 was subjected to the efficacy test as a Newcastle disease vaccine.

1,950 PFU/100 µl/bird of rHVT/NDV were inoculated subcutaneously into the back of fifteen one-day-old SPF chickens (LineM, Japan Biological Laboratories) using 20 Gauge syringe. From three weeks post vaccination onward, the serum was collected from the vaccinated birds and anti-NDV antibody titer was measured by a commercial ELISA kit (IDEXX, ELISA kit to diagnose Newcastle Disease). Chickens of the positive control group were vaccinated at 14 day of age with a commercial NDV live vaccine according to the vender's recommendation. Chickens of the negative control group were not administered with any vaccine. At 43 days of age (42 days post vaccination), chickens of all three groups were challenged with $10^3 EID_{50}$ of NDV-TexasGB, the standard challenge strain in the United States, by intra-muscular route to the femoral region. The challenged chickens were inspected daily to check mortality or to detect any onset of Newcastle disease.

TABLE 3

Challenge experiments of rHVT/NDV-vaccinated SPF chickens with virulent NDV

| Vaccination | Dose (PFU/chicken) | No. of chickens | No. of symptom/total (%) | HI (ELISA) titer at hatch | ELISA titer at challenge |
|---|---|---|---|---|---|
| rHVT/NDV | 1950 | 20 | 0/20 (0) | 0 | 0.207 ± 0.03 |
| Commercial NDV Live vaccine | On label | 10 | 0/10 (0) | | 1.089 ± 0.29 |
| Positive Controls | N/A | 10 | 11/12 (92) | | 0.089 ± 0.01 |
| Negative Controls | N/A | 5 | 0/5 (0) | | N/A |

As shown in Table 3, chickens vaccinated with rHVT/NDV did not show any clinical signs and the ELISA titer at the day of challenge was significantly elevated.

EXAMPLE 6

Efficacy of rHVT/NDV in NDV Maternal Antibody Positive Chickens

To examine the efficacy of rHVT/NDV as a vaccine with anti-NDV maternal antibody positive chickens, fertilized eggs of commercial chickens (Hy-line, Kanagawa Youkei Rengoukai) were purchased and incubated. 1,950 PFU/µl of rHVT/NDV were inoculated into 18-day-old embryos using a 20 Gauge-1.5 inch syringe. Chickens of the positive control group were vaccinated at 14 days of age with a commercial NDV live vaccine according to the vender's recommendation. Chickens of the negative control group were not administered with any vaccine. At 43 days of age, chickens of all groups were challenged with $10^3 EID_{50}$ of NDV-TexasGB, the standard challenge strain in the United States, by intra-muscular route to the femoral region. The challenged birds were inspected daily to check the mortality or to detect any onset of Newcastle disease.

TABLE 4

Challenge experiments of rHVT-vaccinated commercial chickens with virulent NDV

| Vaccination | Dose (PFU/chicken) | No. of chickens | No. of symptom/total (%) | HI (ELISA) titer at hatch | ELISA titer at challenge |
|---|---|---|---|---|---|
| rHVT/NDV | 1950 | 10 | 0/12 (0) | N/A | 0.471 ± 0.108 |
| Commercial NDV Live vaccine | On label | 10 | 0/10 (0) | N/A | 1.386 ± 0.287 |
| Positive Controls | N/A | 10 | 10/10 (100) | N/A | 0.047 ± 0.003 |
| Negative Controls | N/A | 5 | 0/5 (0) | N/A | N/A |

As shown in Table 4, chickens vaccinated with rHVT did not show any clinical sign and ELISA titer at the day of challenge was significantly elevated.

EXAMPLE 7
Co-Relation Between the ELISA Titer and Vaccine Efficacy

Co-relation between the ELISA titer and protection was assessed by measuring the anti-NDV titer in the sera collected at the day of challenge from chickens, which were vaccinated as described in Example 5 and 6. The antibody titer was measured by the commercial ELISA kit described in Example 5. FIGS. 5 and 6 show the ELISA titers of survived or non-survived SPF and commercial birds, respectively. As indicated, all chickens having 0.15 or more of the antibody titer (S/P value) survived the virulent NDV challenge.

EXAMPLE 8

Duration of Immunity

Five chickens vaccinated with rHVT/NDV as described in Example 6 were kept without challenge and every two weeks the NDV-ELISA titers of the collected sera were measured. As a control, non-vaccinated chickens were subjected to the same procedure. The S/P value 0.15, obtained in Example 7, was used as a criterion to determine the protection. The results are shown in Table 5.

TABLE 5

Duration of protective immunity conferred by rHVT/NDV

| Group | | Weeks of age | | | | | | | | | | | |
|---|---|---|---|---|---|---|---|---|---|---|---|---|---|
| | | 2 | 3 | 4 | 5 | 7 | 11 | 15 | 20 | 24 | 30 | 45 | 50 |
| rHVT/NDV | antibody titer | 0.85 | 0.50 | 0.31 | 0.21 | 0.36 | 0.84 | 0.91 | 0.88 | 1.21 | 0.90 | 1.04 | 1.12 |
| | protection | Yes | Yes | Yes | Yes | Yes | Yes | Yes | Yes | Yes | Yes | Yes | Yes |
| Non-vaccinated Controls | antibody titer | 0.74 | 0.46 | 0.10 | 0.03 | −0.01 | 0.02 | 0.05 | 0.02 | 0.02 | 0.00 | 0.01 | 0.02 |
| | protection | Yes | Yes | No | No | No | No | No | No | No | No | No | No |

As shown in Table 5, at 4 weeks of age, the ELISA titer of the non-vaccinated chickens decreased to the value lower than the critical one, indicating no protection. By 50 weeks of age, the titer decreased to nearly zero. On the contrary, the vaccinated chickens showed the lowest titer at 5 weeks of age, which was high enough to confer the complete protection. Afterwards, the value continued to increase gradually to 1.21 at 24 weeks of age, and remained the same until 50 weeks of age. These data indicate that the rHVT/NDV of the present invention is capable of inducing long-lasting protective immunity in the vaccinated maternal antibody-positive commercial birds.

EXAMPLE 9
Isolation of rHVT/NDV from Peripheral Blood Lymphocytes of rHVT/NDV Vaccinated Chickens 3000 PFU of rHVT/NDV was inoculated subcutaneously into the back of a day old anti-NDV maternal antibody positive commercial chickens. The chickens were kept for 30 weeks and every two weeks, peripheral blood was collected from the vein of the wing web of the vaccinated birds. Viruses were recovered from lymphocytes in peripheral blood as described in Example 3. Viruses were recovered from all chickens vaccinated with rHVT/NDV and all viruses were shown to express the F gene.

What is claimed is:

1. A recombinant herpesvirus of turkeys harboring an F protein gene of Newcastle disease virus under the control of a promoter of which sequence is shown in SEQ No.1; wherein said recombinant herpesvirus of turkeys does not comprise an HN gene.

2. A recombinant herpesvirus of turkeys as in claim 1 wherein the promoter and F protein gene are inserted into a noncoding, inter-ORF region of the backbone virus genome.

3. A recombinant herpesvirus of turkeys as in claim 2 wherein the said noncoding region is that located between UL45 and UL46 of the herpesvirus genome.

4. A method of inducing protective immunity in an avian host against avian herpesvirus and Newcastle disease virus, which method comprises inoculating the avian host with the recombinant herpesvirus of turkeys as in claim 1, 2 or 3.

5. A method of inducing protective immunity in an avian host as in claim 4 wherein a recombinant herpesvirus of turkeys is administered to the avian host by subcutaneous or in ovo route.

6. A poultry vaccine comprising a recombinant herpesvirus of turkeys as in claim 1, 2, or 3.

* * * * *

SEQUENCE LISTING

<160> NUMBER OF SEQ ID NOS: 26

<210> SEQ ID NO 1
<211> LENGTH: 555
<212> TYPE: DNA
<213> ORGANISM: Gallus gallus
<220> FEATURE:
<221> NAME/KEY: promoter
<222> LOCATION: (1)..(555)

<400> SEQUENCE: 1

```
gagttattaa tagtaatcaa ttacggggtc attagttcat agcccatata tggagttccg      60
cgttacataa cttacggtaa attggcccgc cggctgaccg cccaacgacc cccgcccatt     120
gacgtcaata atgacgtatg ttcccatagt aacgccaata gggactttcc attgacgtca     180
atgggtggag tatttacggt aaactgccca ttggcagtac atcaagtgta tcatatgcca     240
agtacgcccc ctattgacgt caatgacggt aaatggatgc agtattttgt gcagcgatgg     300
gggcggggggg gggggcgcg cgccaggcgg ggcggggcgg ggcgaggggc ggggcggggc     360
gaggcggaga ggtgcggcgg cagccaatca gagcggcgcg ctccgaaagt ttccttttat     420
ggcgaggcgg cggcggcggc ggccctataa aaagcgaagc gcgcggcggg cgggagtcgc     480
tgcgcgctgc cttcgccccg tgccccgctc cgccgccgcc tcgcgccgcc cgccccggct     540
ctgactgacc gcgtc                                                     555
```

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence:synthetic
      primer DNA for PCR

<400> SEQUENCE: 2

```
cagtgtcgct gcagctcagt gcatgcacgc tcattgccc                             39
```

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence:synthetic
      primer DNA for PCR

<400> SEQUENCE: 3

```
gctctagagt cgacaagctt catggctggc tgcggaggaa cagagaaggg                 50
```

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence:synthetic
      primer DNA for PCR

<400> SEQUENCE: 4

```
tattttgtgc agcgat                                                      16
```

```
<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:synthetic
      primer DNA for PCR

<400> SEQUENCE: 5
acgtctagaa ggcaacgcag cgact                                        25

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:synthetic
      primer DNA for PCR

<400> SEQUENCE: 6
ctgtctagat aacgcggtca gtcaga                                       26

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:synthetic
      primer DNA for PCR

<400> SEQUENCE: 7
ccccgaattc atggaagaaa tttcc                                        25

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence:synthetic
      primer DNA for PCR

<400> SEQUENCE: 8
cgcgggcctt attggccaaa acacacctct aacggttact                        40

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence:synthetic
      primer DNA for PCR

<400> SEQUENCE: 9
gcgcggccaa taaggccaaa acacagtaac cgttagaggt                        40

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence:synthetic
      primer DNA for PCR

<400> SEQUENCE: 10
ccccaagctt tcaagtgata ctgcgtga                                     28
```

```
<210> SEQ ID NO 11
<211> LENGTH: 138
<212> TYPE: DNA
<213> ORGANISM: Artificial Sequence
<220> FEATURE:
<223> OTHER INFORMATION: Description of Artificial Sequence:Modified
      synthetic oligonucleotide from pUC18

<400> SEQUENCE: 11
agcttgccaa taaggctgca ggtcgactct agaggatccc cgggcgagct cgctagcggg      60
cccgcatgcg gtaccgtcga caataaagaa ccgctttaag aatagtgttt attttttgtgt   120 ttatggccaa taaggccg                                                   138

<210> SEQ ID NO 12
<211> LENGTH: 137
<212> TYPE: DNA
<213> ORGANISM: Artificial Sequence
<220> FEATURE:
<223> OTHER INFORMATION: Description of Artificial Sequence:Modified
      synthetic oligonucleotide from pUC18 plasmid

<400> SEQUENCE: 12
aattcggcct tattggccat aaacacaaaa ataaacacta ttcttaaagc ggttctttat      60
tgtcgacggt accgcatgcg ggcccgctag cgagctcgcc cggggatcct ctagagtcga   120
cctgcagcct tattggc                                                   137

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:Synthetic
      primer DNA for PCR

<400> SEQUENCE: 13
tttctgcagt attttgtgca gcgat                                           25

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:Synthetic
      primer DNA for PCR

<400> SEQUENCE: 14
ctgtctagat aacgcggtca gtcaga                                          26

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:Synthetic
      primer DNA for PCR

<400> SEQUENCE: 15
gggctgcaga gttattaata gtaatcaatt                                      30

<210> SEQ ID NO 16
<211> LENGTH: 30
<212> TYPE: DNA
<213> ORGANISM: Artificial Sequence
```

```
<220> FEATURE:
<223> OTHER INFORMATION: Description of Artificial Sequence:Synthetic
      primer DNA for PCR

<400> SEQUENCE: 16
gggatgcatc catttaccgt cattgacgtc                                          30

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:Synthetic
      primer DNA for PCR

<400> SEQUENCE: 17
gggtcgttgg gcggtcagcc ggcgg                                               25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:Synthetic
      primer DNA for PCR

<400> SEQUENCE: 18
cttacggtaa atggcccgcc ggctg                                               25

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:Synthetic
      primer DNA for PCR

<400> SEQUENCE: 19
tacacttgat gtactgccaa gggc                                                24

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence:Synthetic
      primer DNA for PCR

<400> SEQUENCE: 20
tatttacggt aaactgccca ttggc                                               25

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence:Synthetic
      primer DNA for PCR

<400> SEQUENCE: 21
gctctagagg atccgcatgg gctccagatc ttctaccagg atccc                         45

<210> SEQ ID NO 22
<211> LENGTH: 34
<212> TYPE: DNA
<213> ORGANISM: Artificial Sequence
```

-continued

```
<220> FEATURE:
<223> OTHER INFORMATION: Description of Artificial Sequence:Synthetic
      primer DNA for PCR

<400> SEQUENCE: 22
gcgagctcgg tccatgactg aagactgcta ttgg                               34

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence:Synthetic
      primer DNA for PCR

<400> SEQUENCE: 23
ctagcagtgg cagttgggaa gat                                          23

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:Synthetic
      primer DNA for PCR

<400> SEQUENCE: 24
gttaaggcag gggaagtgat ttgt                                         24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:Synthetic
      primer DNA for PCR

<400> SEQUENCE: 25
ggggaagtct tccggttaag ggac                                         24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence:Synthetic
      primer DNA for PCR

<400> SEQUENCE: 26
ggtgcaattc gtaagaccga tggg                                         24
```